(12) United States Patent
Seppi et al.

(10) Patent No.: US 7,369,640 B2
(45) Date of Patent: *May 6, 2008

(54) RADIATION SCANNING OF OBJECTS FOR CONTRABAND

(75) Inventors: Edward J. Seppi, Portola Valley, CA (US); Marcel Marc, San Jose, CA (US); John Ford, Madison, TN (US)

(73) Assignee: Varian Medical Systems Technologies, Inc., Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/515,479

(22) Filed: Sep. 1, 2006

(65) Prior Publication Data

US 2007/0003003 A1    Jan. 4, 2007

Related U.S. Application Data

(63) Continuation of application No. 10/202,273, filed on Jul. 24, 2002, now Pat. No. 7,103,137.

(51) Int. Cl.
*G01N 23/00* (2006.01)

(52) U.S. Cl. .......................................... 378/9; 378/57
(58) Field of Classification Search .................... 378/9, 378/10, 57, 58
See application file for complete search history.

(56) References Cited

U.S. PATENT DOCUMENTS

| | | | |
|---|---|---|---|
| 3,018,374 A | 1/1962 | Pritchett | |
| 3,636,353 A | 1/1972 | Untermyer | |
| RE28,544 E | 9/1975 | Stein et al. | |
| 3,924,132 A | 12/1975 | Koslow | |
| 4,031,545 A | 6/1977 | Stein et al. | |
| 4,149,081 A | 4/1979 | Seppi | |
| 4,196,352 A * | 4/1980 | Berninger et al. | ............. 378/7 |

(Continued)

FOREIGN PATENT DOCUMENTS

WO    WO 96/13839    5/1996

OTHER PUBLICATIONS

McDonald, Marci; "Checkpoint Terror Border Searches Snarl the Free Flow of Goods" U.S. News and World Report, p. 52, Feb. 11, 2002.

(Continued)

*Primary Examiner*—Jurie Yun
(74) *Attorney, Agent, or Firm*—Brandon N. Sklar; Kaye Scholer LLP

(57) ABSTRACT

In one example, a scanning unit for examining contents of a cargo container is disclosed comprising a first path through the scanning unit for transport of a cargo container and one or more sources of respective beams of radiation. At least one of the one or more sources are movable across a second path transverse to the first path. The second path extends partially around the first path. The scanning unit further comprises a detector extending partially around the first path. The detector is positioned to detect radiation interacting with the cargo container during scanning, such as radiation transmitted through the container. The at least one source and the detector are positioned so that the cargo container is transportable along the first path, between the source and the detector. A transport system may be provided to convey the object through the scanning unit, along the first path.

54 Claims, 8 Drawing Sheets

U.S. PATENT DOCUMENTS

| | | | |
|---|---|---|---|
| 4,229,654 A | 10/1980 | Arya et al. |
| 4,251,726 A | 2/1981 | Alvarez |
| 4,352,021 A | 9/1982 | Boyd et al. |
| 4,357,535 A | 11/1982 | Haas |
| 4,430,568 A | 2/1984 | Yoshida et al. |
| 4,521,900 A | 6/1985 | Rand |
| 4,599,740 A | 7/1986 | Cable |
| 4,631,741 A | 12/1986 | Rand et al. |
| 4,671,256 A | 6/1987 | Lemelson |
| 4,722,096 A | 1/1988 | Dietrich et al. |
| 4,918,315 A | 4/1990 | Gomberg et al. |
| 4,941,162 A | 7/1990 | Vartsky et al. |
| 4,956,856 A | 9/1990 | Harding |
| 4,987,584 A | 1/1991 | Doenges |
| 5,044,002 A | 8/1991 | Stein |
| 5,065,418 A | 11/1991 | Bermbach et al. |
| 5,076,993 A | 12/1991 | Sawa et al. |
| 5,098,640 A | 3/1992 | Gozani et al. |
| 5,115,459 A | 5/1992 | Bertozzi |
| 5,124,554 A | 6/1992 | Fowler et al. |
| 5,153,439 A | 10/1992 | Gozani et al. |
| 5,200,626 A | 4/1993 | Schultz et al. |
| 5,278,418 A | 1/1994 | Broadhurst |
| 5,313,511 A | 5/1994 | Annis et al. |
| 5,367,552 A * | 11/1994 | Peschmann ................ 378/57 |
| 5,410,156 A | 4/1995 | Miller |
| 5,420,905 A | 5/1995 | Bertozzi |
| 5,490,218 A | 2/1996 | Krug et al. |
| 5,491,734 A | 2/1996 | Boyd et al. |
| 5,493,596 A | 2/1996 | Annis |
| 5,495,106 A | 2/1996 | Mastny |
| 5,524,133 A | 6/1996 | Neale et al. |
| 5,557,108 A | 9/1996 | Tumer |
| 5,600,303 A | 2/1997 | Husseiny et al. |
| 5,600,700 A | 2/1997 | Krug et al. |
| 5,611,502 A | 3/1997 | Edlin et al. |
| 5,638,420 A | 6/1997 | Armistead |
| 5,642,394 A | 6/1997 | Rothschild |
| 5,692,028 A | 11/1997 | Geus et al. |
| 5,692,029 A | 11/1997 | Husseiny et al. |
| 5,696,806 A | 12/1997 | Grodzins et al. |
| 5,729,582 A | 3/1998 | Ham et al. |
| 5,818,054 A | 10/1998 | Randers-Pehrson et al. |
| 5,838,758 A | 11/1998 | Krug et al. |
| 5,838,759 A | 11/1998 | Armistead |
| 5,841,832 A | 11/1998 | Mazess et al. |
| 5,917,880 A | 6/1999 | Bjorkholm |
| 5,930,326 A | 7/1999 | Rothschild et al. |
| 5,966,422 A | 10/1999 | Dafni et al. |
| 5,974,111 A | 10/1999 | Krug et al. |
| 6,018,562 A | 1/2000 | Willson |
| 6,041,097 A | 3/2000 | Roos et al. |
| 6,078,642 A | 6/2000 | Simanovsky et al. |
| 6,088,423 A | 7/2000 | Krug et al. |
| 6,151,381 A | 11/2000 | Grodzins et al. |
| 6,218,943 B1 | 4/2001 | Ellenbogen |
| 6,236,709 B1 | 5/2001 | Perry et al. |
| 6,249,567 B1 | 6/2001 | Rothschild et al. |
| 6,259,762 B1 | 7/2001 | Pastyr et al. |
| 6,269,142 B1 | 7/2001 | Smith |
| 6,278,115 B1 | 8/2001 | Annis et al. |
| 6,292,533 B1 | 9/2001 | Swift et al. |
| 6,347,132 B1 | 2/2002 | Annis |
| 6,411,674 B1 | 6/2002 | Oikawa |
| 6,438,201 B1 * | 8/2002 | Mazess et al. ................ 378/56 |
| 6,449,334 B1 | 9/2002 | Mazess et al. |
| 6,490,337 B1 | 12/2002 | Nagaoka et al. |
| 6,628,745 B1 * | 9/2003 | Annis et al. ................ 378/21 |
| 6,687,328 B2 | 2/2004 | Bavendiek et al. |
| 6,965,661 B2 * | 11/2005 | Kojima et al. ................ 378/4 |
| 7,103,137 B2 * | 9/2006 | Seppi et al. ................ 378/9 |

OTHER PUBLICATIONS

Grodzins, Lee: Nuclear Techniques For Finding Chemical Explosives in Airport Luggage: Beam Interactions With Materials and Atoms; May 1991; p. 829-833; vol. B56/57, Part II; Elsevier Science Publishers B.V. (North-Holland); Holland.

* cited by examiner

RADIATION SCANNING OF OBJECTS FOR CONTRABAND

The present application is a continuation of U.S. patent application Ser. No. 10/202,273, which was filed on Jul. 24, 2002, will issue on Sep. 5, 2006 bearing U.S. Pat. No. 7,103,137, is assigned to the assignee of the present invention and is incorporated by reference herein.

FIELD OF THE INVENTION

Radiation scanning of objects, including large objects such as cargo containers, to identify contraband.

BACKGROUND OF THE INVENTION

Radiation is commonly used in the non-invasive inspection of objects such as luggage, bags, briefcases and the like, to identify hidden contraband at airports and public buildings. The contraband may include hidden guns, knives, explosive devices and illegal drugs, for example. One common inspection system is a line scanner, where the object to be inspected is passed between a stationary source of radiation, such as X-ray radiation, and a stationary detector. The radiation is collimated into a fan beam or a pencil beam. Radiation transmitted through the object is attenuated to varying degrees by the contents of the luggage. The attenuation of the radiation is a function of the density of the materials through which the radiation beam passes. The attenuated radiation is detected and radiographic images of the contents of the object are generated for inspection. The images show the shape, size and varying densities of the contents.

To obtain additional information about the contents of the luggage, detectors may be provided to detect scattered radiation, as described in U.S. Pat. No. 5,642,394, for example. Systems may combine detection of scattered radiation with the detection of transmitted radiation.

Another technique to enhance the information that may be derived about the material composition of the contents of the objects is to scan the object with radiation beams having two different energy levels. A ratio of the attenuation detected at two energy levels is indicative of the atomic numbers of the material through which the radiation beam passes. Dual energy systems enable better detection of plastic materials and illegal drugs.

One disadvantage of radiographic imaging is that all items within the object in the path of the radiation beam are superimposed on the image. If there are many items in the object, it may be difficult to distinguish among them. The identification of dangerous items is thereby hampered. In addition, the orientation and shape of the items within the object could effect whether they can be identified on a radiograph. Thin sheets of explosive materials may also be difficult to identify on a radiograph, particularly if they are oriented perpendicular to the scanning beam.

Computed tomography ("CT") enables the reconstruction of the cross-sectional images of luggage contents, facilitating the identification of the items in the luggage. CT images also provide higher resolution, greater image contrast and greater sensitivity to characteristics of the object being scanned, than radiographs. However, reconstruction of CT images of an object requires a large number of scans of the object at a plurality of angles. Conducting a sufficient number of scans for CT reconstruction is time consuming. Depending on the system used, CT imaging of an entire piece of luggage may be too slow for practical use in screening luggage in airports, for example.

In U.S. Pat. No. 5,367,552 ("the '552 patent"), a source of X-ray radiation is provided on one side of an inner surface of a rotating module and a detector array is provided on the opposite side. Luggage is moved through the module incrementally. The module rotates to scan the luggage at a plurality of angles, at each incremental position. The inspection speed may be increased by pre-screening with a line-scan. Then, only suspicious regions identified by the pre-screening step are subjected to CT imaging.

U.S. Pat. No. 6,078,642 ("the '642 patent) discloses a CT scanning system for luggage where data processing techniques are used to speed the inspection rate. As in the '552 patent, an X-ray source and a detector array are disposed on opposing sides of a rotating module. The source may emit a pyramidal cone beam of radiation and the detector array may be 2-dimensional. The module rotates as a piece of luggage is continuously moved through the module, providing helical volumetric CT scanning. CT scanning is said to be provided of the entire piece of luggage, without requiring pre-scanning. The source may emit an X-ray beam of two different energy distributions, as well.

While the smuggling of contraband such as guns and explosives onto planes in carry-on bags and in luggage has been a well known, ongoing concern, a less publicized but also serious threat is the smuggling of contraband across borders and by boat in large cargo containers. Only 2%-10% of the 17 million cargo containers brought to the United States by boat are inspected. "Checkpoint terror", U.S. News and World Report, Feb. 11, 2002, p. 52.

Standard cargo containers are typically 20-50 feet long (6.1-15.2 meters), 8 feet high (2.4 meters) and 6-9 feet wide (1.8-2.7 meters). Air cargo containers, which are used to contain a plurality of pieces of luggage or other cargo to be stored in the body of an airplane, may range in size (length, height, width) from about 35×21×21 inches (0.89×0.53× 0.53 meters) up to about 240×118×96 inches (6.1×3.0×2.4 meters). Large collections of objects, such as many pieces of luggage, may also be supported on a pallet. Pallets, which may have supporting side walls, may be of comparable sizes as cargo containers and use of the term cargo container will generally encompass pallets, as well.

In contrast to the cargo container size ranges, typical airport scanning systems for carry-on bags have tunnel entrances up to about 0.40×0.60 meters. Scanning systems for checked luggage have travel openings that are only slightly larger. Since only bags that fit through the tunnel may be inspected, such systems cannot be used to inspect cargo containers. The low energies used in typical X-ray luggage and bag scanners, described above, are also too low to penetrate through the much larger cargo containers. In addition, many such systems are too slow to economically inspect larger objects, such as cargo containers.

U.S. Pat. No. 6,292,533 B1 discloses a mobile X-ray inspection system for large objects, such as a cargo container carried by a vehicle, that uses an X-ray source of 450 kV. The source is supported on a truck and a pencil beam is generated to vertically scan the vehicle. Detectors, also supported on the truck or a boom extending from the truck, are provided to detect radiation transmitted through and scattered by the contents of the object. In use, a vehicle to be inspected parks alongside the scanning unit on the truck. The source and detectors are moved horizontally by a translation system within the truck to horizontally scan the vehicle. While having sufficient penetration, use of a pencil beam may be too slow to efficiently scan cargo containers. The scan motion is said to be "exceedingly slow" (⅓-⅙ of a mile per hour).

U.S. Pat. No. 5,917,880 discloses an X-ray inspection apparatus that may be used to inspect cargo containers, that uses X-ray radiation of about 8 MeV, collimated into a vertical fan beam to scan a truck carrying the cargo. A first detector array is aligned with the fan beam to detect radiation transmitted through the truck. A second detector array is provided to detect radiation forward scattered through the truck. The truck is moved through the vertical fan beam. Data from both detectors is used to determine the average atomic number of the attenuating material in the truck to identify the material content in the truck. Images indicative of the material content are then prepared. Data provided by the first detector array is also used to form radiographs of the truck. While faster than a pencil beam, a fan beam may still be too slow to efficiently scan large objects at a reasonable rate.

In U.S. Pat. No. 5,638,420, large containers are inspected by a system on a movable frame. A source of a fan beam, a cone beam or a pencil beam of X-ray radiation, such as a linear accelerator with an accelerating potential in the MV range, is mounted on one side of the frame. A detector array is mounted on an opposing side of the frame. The frame may be self-propelled and advances across the length of the container. Radiographic images are generated for analysis by an operator.

Radiographic images of large objects such as cargo containers suffer from the same problems described above with respect to radiographic images of smaller objects such as luggage. U.S. Pat. No. 5,524,133 discloses scanning systems for large objects such as freight in a container or on a vehicle. In one embodiment, two stationary sources of X-ray radiation are provided, each emitting a beam that is collimated into a fan beam. The sources facing adjacent sides of the freight and the fan beams are perpendicular to each other. A stationary detector array is located opposite each source, on opposite sides of the freight, to receive radiation transmitted through the freight. In addition, X-ray radiation of two different energies are emitted by each source. One energy is significantly higher than the other. For example, energies of 1 MeV and 5 or 6 MeV may be used. A ratio of the mean number of X-rays detected at each energy level by the detector array as a whole for each slice or by the individual detectors of the array is determined and compared to a look up table to identify a mean atomic number corresponding to the ratio. The material content of the freight is thereby determined. Three dimensional images based on the ratios of mean atomic number may be reconstructed from the data collected by both detector arrays. The patent states that while the images are coarse, they enable the shapes of certain items to be determined. In combination with the determination of the mean atomic number of the materials in those items, suspicious items may be eliminated or flagged for further inspection.

While three dimensional images based on radiographs are an improvement over radiographs themselves, the high resolution, improved image contrast and the ability to distinguish small differences in characteristics of items within in an object that are provided by CT scanning would be advantageous in the inspection of cargo containers. The CT scanning units used in airports for luggage and the like discussed above are not readily scaleable to the large sizes required to scan cargo containers. For example, to accommodate a cargo container, the rotating modules of the '552 patent or the '642 patent would need to be greatly enlarged. Such large rotating units, carrying both the sources and the detectors, would be very expensive and would be difficult to operate and maintain.

In medical CT scanning, there is a configuration referred to as fourth generation, wherein a source of X-ray radiation rotates completely around a patient in a path of a circle within a larger, stationary circular detector array. Fourth generation CT scanners have been found to be an improvement over earlier generations of scanners where both the source and the detector arrays are moved. Scanning times are shorter and the construction of the scanner is simpler. The arrangements of sources and detectors in medical CT scanners are described in more detail in Seeram, Euclid, *Computed Tomography: Physical Principles, Clinical Applications, and Quality Control*, Second Edition, W.B. Saunders Company, (2001), pp. 10, 77-81. While only the source is moved completely around the patient, enlargement of such a system to accommodate large objects such as cargo containers would still be difficult.

Despite the various designs for the inspection of large objects such as cargo containers disclosed in the patents discussed above and in other references, much of the inspection of cargo containers is done manually, if at all. "Checkpoint terror", U.S. News and World Report, Feb. 11, 2002, p. 52. Practical, efficient, non-intrusive radiation scanners for the inspection of large objects, such as cargo containers, are still needed. The ability to perform CT imaging of large objects is needed, as well.

SUMMARY OF THE INVENTION

In accordance with one embodiment of the present invention, a scanning unit for examining contents of a cargo container is disclosed comprising a first path through the scanning unit for transport of a cargo container and one or more sources of respective beams of radiation. At least one of the one or more sources are movable across a second path transverse to the first path. The second path extends partially around the first path. The scanning unit further comprises a detector extending partially around the first path. The detector is positioned to detect radiation interacting with the cargo container during scanning. The at least one source and the detector are positioned so that the cargo container is transportable along the first path, between the source and the detector. A transport system may be provided to convey the object through the scanning unit, along the first path. The cargo container may be supported by a vehicle and the detector and the at least one source of radiation are then positioned to allow the cargo container and the vehicle to be transported therebetween.

The detector may be stationary. The detector may be positioned to detect radiation transmitted through the cargo container. The at least one source and the detector may be positioned to scan a cargo container having a height and/or width of at least about 1.5 meters. During operation, the detector may be positionable, at least in part, beneath the first path, below ground, and the at least one source may be positionable above the first path. The scanning unit may comprise at least one energy sensitive detector.

The second path may be arcuate. An arcuate rail may be provided along the arcuate second path and the at least one source may be coupled to the arcuate rail. The at least one source may be movable with respect to the rail or the rail may be movable to move the at least one source along the second path. The second path may be at least partially circular and the arcuate rail may form at least part of a circle.

A processor may be coupled to the detector. The processor may be programmed to reconstruct computed tomography images based, at least in part, on data received from the detector. The second path and the detector may extend sufficiently around the object to collect sufficient data for computed tomographic imaging.

The at least one source may be a linear accelerator. The at least one source may be mechanically movable across the second path. A plurality of sources may be provided, each being mechanically movable across a single, common path. The at least one source may be adapted to generate radiation of at least 1 MeV.

The one or more sources may be adapted to scan the cargo container with two different energy distributions. At least one of the one or more sources may be operational to selectively switch between emitting radiation having a first energy distribution and radiation having a second energy distribution different than the first energy distribution. At least one of the one or more sources may emit radiation having a first energy distribution and at least one of the one or more sources may emit radiation having a second energy distribution different than the first energy distribution. A second, energy sensitive, detector may be provided, between the second detector and the at least one source. A processor may be electrically coupled to the first detector and the second detector. The processor may be programmed to reconstruct computed tomography images based on data received from the first detector, reconstruct energy based images based on data received from the second detector, and fuse the images based on data from the first detector with the images based on the data received from the second detector.

In accordance with another embodiment, a method of examining contents of a cargo container is disclosed comprising moving at least one radiation source with respect to a cargo container, scanning at least a portion of the cargo container with at least one radiation beam from the at least one radiation source at a plurality of angles, detecting radiation interacting with the cargo container, and reconstructing images based, at least in part, on the detected radiation. Data may be processed based on the detected radiation to form computed tomographic images of at least the portion of the cargo container. The at least one source may be moved along a path in a second direction transverse to the first direction. Radiation transmitted through the cargo container may be detected by a stationary detector in a first direction and the cargo container may have a height and/or width of at least about 1.5 meters. The cargo container may be supported by a vehicle during scanning.

The cargo container may be scanned with a radiation beam having a first energy distribution and with a radiation beam having a second energy distribution different from the first energy distribution. Radiation may be detected with a first, spatial detector, and with a second, energy sensitive, detector. Data may be processed based on the detected radiation from the first and second detectors to form respective computed tomographic images of the cargo container. Corresponding computed tomographic images from the radiation detected from the first and second detectors may be fused.

The at least one source may be moved along a single arc extending only partially around the cargo container. The one or more sources may be moved along a rail. The rail may extend only partially around the object.

In accordance with another embodiment of the invention, a scanning unit for examining contents of a cargo container is disclosed comprising a first path through the scanning unit for transport of a cargo container and one or more sources of respective beams of radiation. At least one of the one or more sources is movable across a second path transverse to the first path. The second path extends at least partially around the first path. A detector extends at least partially around the first path. The detector is positioned to detect radiation interacting with the cargo container during scanning. The at least one source and the detector are positioned so that the cargo container is transportable along the first path, between the source and the detector.

As used herein, the term "cargo container" encompasses pallets.

DESCRIPTION OF THE PREFERRED EMBODIMENTS

Figure 1:
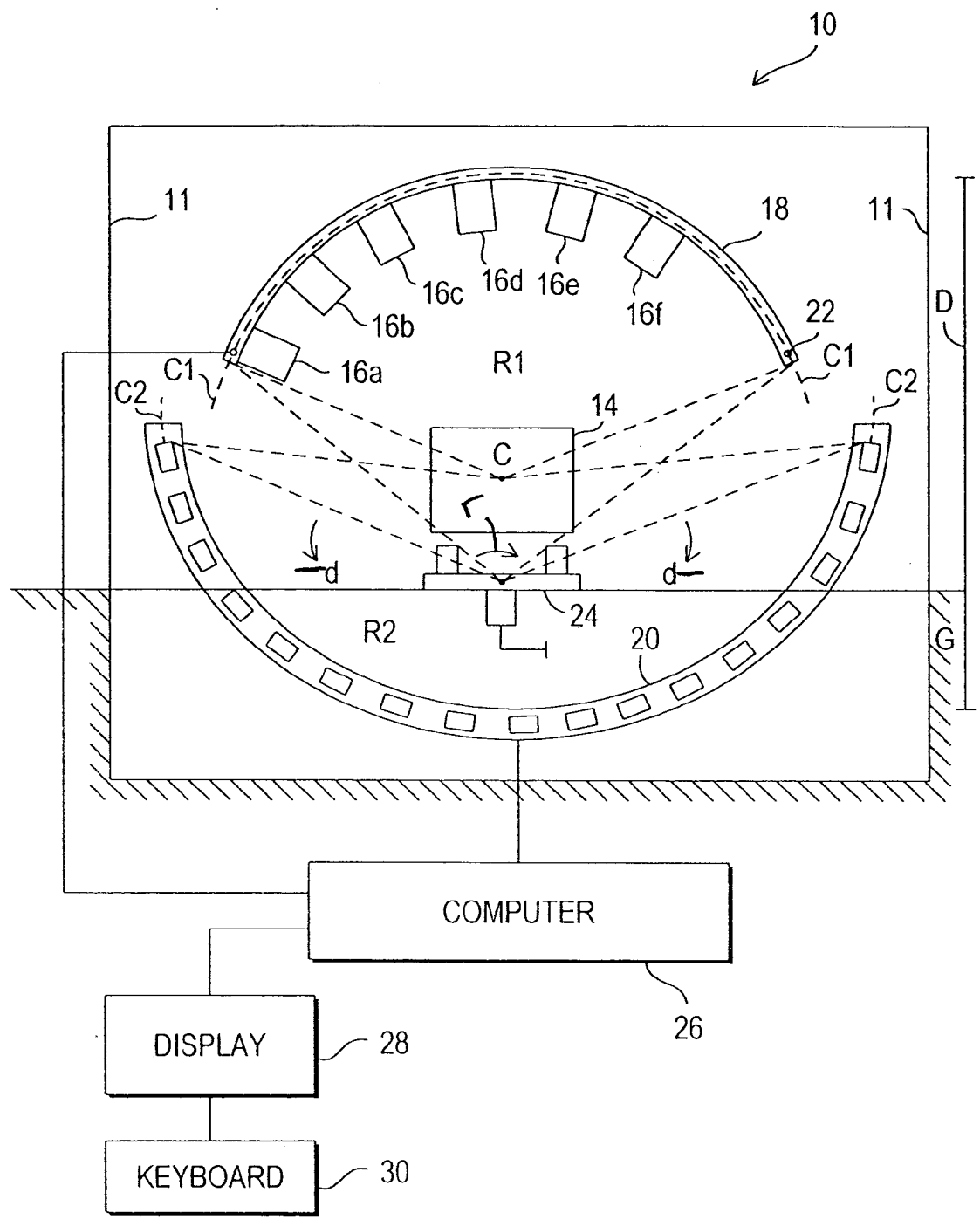
FIG. 1 is a front schematic view of an interior of a cargo scanning unit in accordance with one embodiment of the invention.
Figure 2:
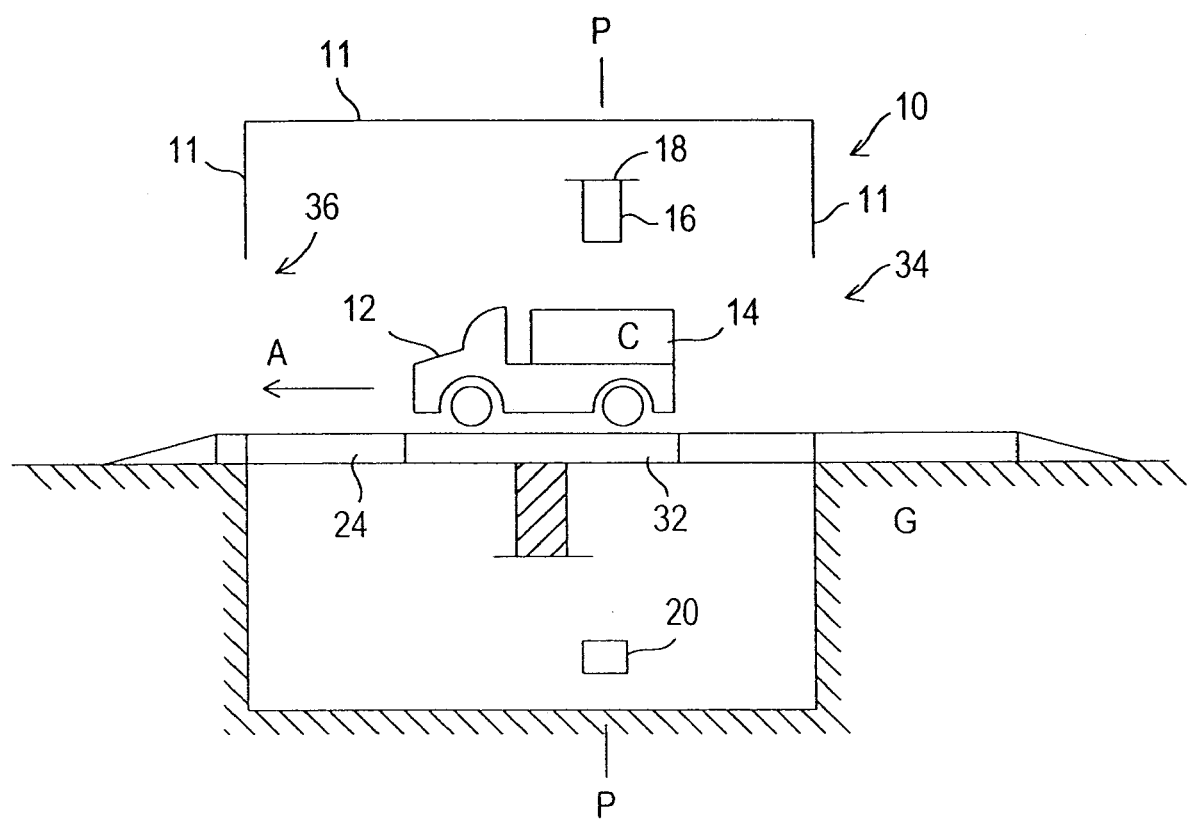
FIG. 2 is a side, interior view of the scanning unit of FIG. 1, showing the truck being moved through the unit, along the direction of arrow "A"

FIG. 1 is a front schematic view of an interior of a cargo scanning unit 10 for inspecting objects for contraband, such as explosive devices and materials, in accordance with one embodiment of the invention. FIG. 2 is a side schematic view of the center of the interior of the cargo scanning unit 10. The objects can be small objects, such as luggage and bags, or large objects, such as cargo containers. The scanning unit 10 comprises shielded walls 11. In FIG. 1, a truck 12 carrying a cargo container 14 is shown moving through the scanning unit 10, out of the page, along a first path. In FIG. 2, the direction of the first path is indicated by arrow "A".

Figure 3:
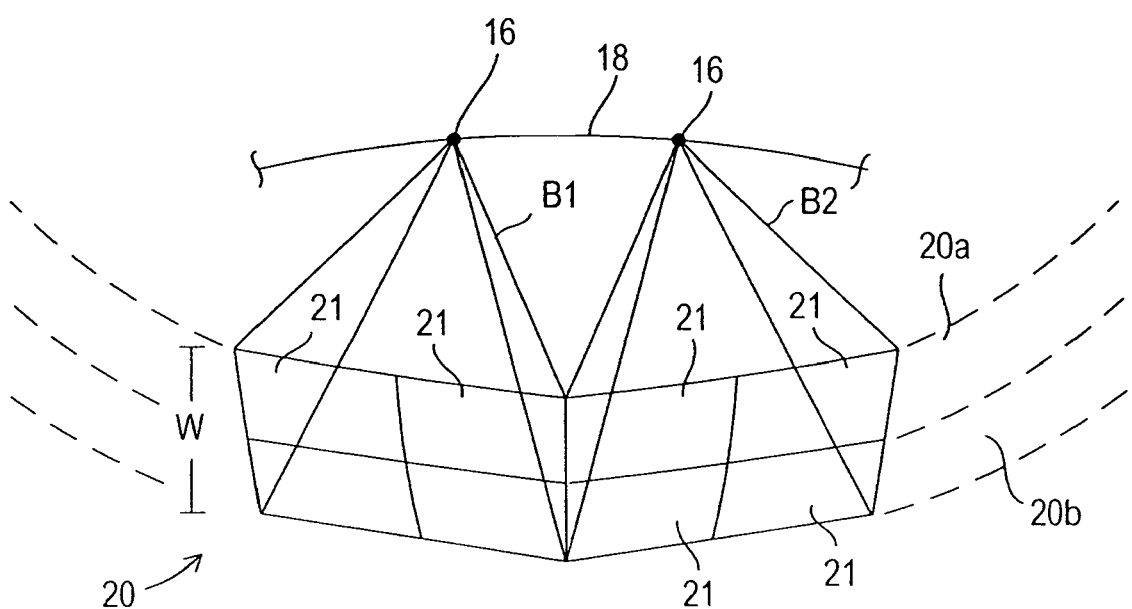
FIG. 3 is a schematic representation of two asymmetric cone beams emitted by adjacent X-ray sources, illuminating a portion of a detector array.

In this embodiment, the scanning unit 10 comprises six X-ray sources 16a-16f, a rail 18 supporting each of the X-ray sources 16a-16f and a detector 20. The detector 20 may be a detector array comprising a plurality of detector modules 21, as shown in FIG. 3, for example. The rail 18 and the detector array 20 lie along the same plane "P", identified in FIG. 2, to detect radiation emitted by the sources 16a-16f after passing through the cargo container 13. The plane P is transverse to the first direction A along the first path. In this embodiment, the plane P is perpendicular to the first direction A and to the first path.

A conveying system 22 is provided to move the X-ray sources 16 along the rail 18 and/or to move the rail.

The X-ray sources 16*a*-16*f* and/or the rail are moved within a region R1 extending only partially around the first path A. Therefore, the sources 16*a*-16*f* are not moved completely around the path A (or the cargo container 14). Similarly, the detector array 20 lies within a region R2 extending only partially around the first path A. The detector array 20 does not extend completely around the cargo container 14, either. In the embodiment of FIG. 1, the Regions R1 and R2 are wholly separate, although there may be some overlap, if desired.

In the embodiment of FIG. 1, the rail 18 is semi-circular and lies on a first imaginary circle C1 with a center that is at or close to the center C of the cargo. Similarly, in this embodiment, the detector array 20 is also semi-circular and lies on a second imaginary circle C2 with a center at or close to the center C of the cargo. While in the embodiment of FIG. 1, the first and second imaginary circles are not the same, they may be. The first and second imaginary circles both lie in the same plane P. The detector array 20 may be straight or have other shapes, as well. The extents of the arcs of the semi-circular rail 18 and detector array 20 depend on the characteristics of the beams emitted by the sources 16*a*-16*f*, as discussed further below.

The sources 16*a*-16*f* and the detector array 20 are arranged and spaced a sufficient distance "D" so that the truck 12 and cargo container 14 may pass between them. For a typical cargo container 14 of 20×8×8 feet (6.1×2.4×2.4 meters) supported by a typical truck 12, a distance D of about 25 feet (7.62 meters) may be provided.

A transport system 24, such as a moving belt connected to the truck 12 or a track along the path A, may be provided to move the truck through the cargo scanning unit 10 along the path A. The belt or track may be driven by one or more motors (not shown).

The cargo container 14 need not be supported by the track 12. The cargo container 14, or other such object to be inspected, may be directly supported and conveyed by the transport system 24. The motor driven belt or track may also be used to directly convey the cargo container 14. Mechanically driven rollers may also be used.

The detector array 20 detects X-rays transmitted through the cargo container 14. The detector array 20 is electrically connected to a processor 26, such as a computer, which reconstructs the data output by the detector array 20 into images, as discussed further below. Analog-to-digital converting devices and other electronic components are provided as required. The computer 26 is connected to a display 28 that displays the reconstructed images. The computer 26 may store the reconstructed images in a database, along with identifying information about each truck 12 or cargo container 14, such as the license plate, and other useful information, such as the date that the truck is scanned. The operator of the scanning unit 10 can enter the relevant information though a keyboard 30 or the information can be scanned or otherwise entered automatically. The computer 26 is also connected to the X-ray sources 16 to control their operation, to the conveyor system 22 to control movement of the sources 16 and/or the rail 18 and to the transport system 24. Multiple processors or computers may be used, as well.

The transport system 24 may include a vertical platform 32, shown in FIG. 2, to lift or lower the truck 12 as necessary to position the center C of the cargo container 14 at or near the center of the imaginary circles of the rail 18 and the detector array 20, under the control of the computer 26. An entrance 34 and exit 36 of the scanning unit 10 are shown, as well.

The conveyor system 22 moves all the sources 16 simultaneously, in one direction and then in the opposite direction, to enable scanning of the entire volume of the cargo container 14 at a plurality of angles. The conveyor system 24 may comprise a motor driven closed chain (not shown) supported by the rail 18. The X-ray sources 16 may be supported by the rail 18 and moved by the chain by gears, for example, coupled to the motor. The motor may be controlled by the computer 26 to move the chains first in one direction, then in the opposite direction, continuously or in discrete intervals. Depending on the length of the rail 18, the rail itself can be moved, instead of or in addition to moving the sources 16, by providing an appropriate supporting and conveying system for the rail. The conveying system 22 for the rail 18 may be a mechanically driven track or mechanically driven rollers, as well.

The X-ray source 16 may be a source of Bremstrahlung radiation, for example. To examine cargo containers having a width greater than about 5 feet (1.5 meters) by a scanning unit 10 in accordance with the embodiment of FIG. 1, the X-ray source may generate radiation having an energy distribution with an average energy greater than about 1 MeV. The X-ray source 16 may generate radiation having an energy distribution with an average energy greater than about 6 MeV, for example. The X-ray source 16 may be a linear accelerator, such as a Linatron® Linear Accelerator ("Linatron®"), having an accelerating potential in a range of about 6 MV or more, available from Varian Medical Systems, Inc., Palo Alto, Calif. ("Varian"), for example. In the Varian Linatron®, 360 pulses are output per second. The Varian Linatron® has an opening angle of about 20-30 degrees, for example. Other X-ray sources may be used as well, such as electrostatic accelerators, microtrons and betatrons, for example. X-ray tubes may also be used, particularly for objects having a width less than about 5 feet (1.5 meters).

If Varian Linatrons® are used as the sources 16 in the configuration of FIG. 1, six sources may be provided, equidistantly spaced on the semi-circular rail 18, to illuminate a pie-shaped region of about 120 degrees of the cargo container 14. The emissions of each source 16 are synchronized with the detector or detectors of the detector array 20 that each source illuminates, by the computer 26. The emissions of the sources 16 may or may not be synchronized with each other to emit pulses simultaneously. The sources may emit radiation at angles up to about 180 degrees, which can be collimated to any desired shape, such as a cone or fan beam. The radiation beam can be emitted from a point, as in a linear accelerator, along a line or from a two-dimensional area.

One or more collimators (not shown) may be provided between each of the X-ray sources 16 and the cargo container 14 to collimate the X-ray beam from each source 16 into a cone beam. The cone beam may be an asymmetric rectangular cone, for example. Two adjacent asymmetric rectangular cone beams B1, B2 are shown in FIG. 3. The use of rectangular cone beams avoids exposure of the cargo to excessive radiation that is not used in imaging the cargo container. It also minimizes scattered radiation that may be detected, improving image quality. A circular cone beam could be used but data collected from portions of the cone beam proximate the boundary of the circle would typically be discarded. Other shaped cone beams could be used, as well.

The cone beam need not be a mathematical cone; it may be an arbitrarily shaped cone. Here, "cone beam" refers to an X-ray beam having longitudinal and lateral dimensions to illuminate a two dimensional detector, as described further, below. A cone beam is used in this embodiment because a cone beam can uniformly scan a larger volume of the cargo container per scan, as compared to a fan beam or a pencil beam, decreasing the time required to scan the entire cargo container 14.

Collimators (not shown) may also be provided between the cargo container 14 and the detector array 20 to block scattered radiation from reaching the detectors 21 of the detector array.

When the X-ray radiation is in the form of a cone beam, the detector array 20 may comprise one or more rows of two dimensional detector modules to detect X-ray transmission through the cargo container 14. In FIG. 3, two rows 20a, 20b of detector modules 21 are shown. Each X-ray source 16, shown schematically as a point source on the rail 18, is aimed at a different detector module or modules 21, of the detector array 21, as shown. In FIG. 3, each cone beam B is aimed at a rectangular group of four detector modules. The detector modules 21 are shown enlarged and the cargo container 14 is not shown in FIG. 3, for ease of illustration. Each two-dimensional detector module 21 comprises a plurality of rows and columns of detector elements, such as photosensitive elements, in a housing. The components of the modules, which are known in the art, are not shown. The photosensitive elements may be photodiodes, for example. If a fan beam is used, a single row of one-dimensional detectors (comprising a single row of detector elements) may be used.

The scanning unit 10 may be used to obtain radiographic images or computed tomography ("CT") images. In order to obtain a complete data set for CT reconstruction, either the sources 16a-16f should be moved across an arc or the detector array 20 should extend over an arc, equal to 180° plus the lateral arc of the emitted X-ray beams. For example, if the lateral arc of the beam is about 30°, the arc of the movement of the sources 16a-16f or the arc of the detector array 20 should be about 210°. The arc of the other component should then be about 180°. Alternatively, the arc of both may be about 200°.

The longitudinal or axial width of each cone beam emitted by each source 16a-16f at the detector array 20 may approximately correspond to the width "W" of the detector array, as shown in FIG. 3. The lateral length of each cone beam depends on the number of sources and the lateral length of the detector array 20. In FIG. 3, each cone beam is shown illuminating a lateral length "L" of the detector array 20 comprising two detectors. The lateral lengths of the cone beams may be adjusted so that the adjacent cone beams overlap portions of the detector array 20, to ensure that all the detectors 21 are illuminated.

To simplify analysis of detected signals and reconstruction of images, in one embodiment, only the sources 16a-16f that project X-ray beams that do not overlap on the same detector 21 of the detector array 20 are on at the same time. For example, only one of the sources 16a-16f may be on at a time. Data acquisition may be increased by turning multiple sources on concurrently. Where the lateral length of each cone beam is adjusted so that adjacent beams overlap on the detector array 20, the pairs of sources 16a and 16d, 16b and 16e and 16c and 16f may be on at the same time, for example. For even faster data acquisition, the sources 16a, 16c and 16e may be on at the same time and the sources 16b, 16d and 16f may also be on at the same time. The groups of sources may be cycled on in succession as the sources 16a-16f are moved across the rail 18, under the control of the computer 26. Data from detector modules 21 that are not aligned with a source which is on may be rejected, unless information from scattered radiation is desired.

Figure 4:
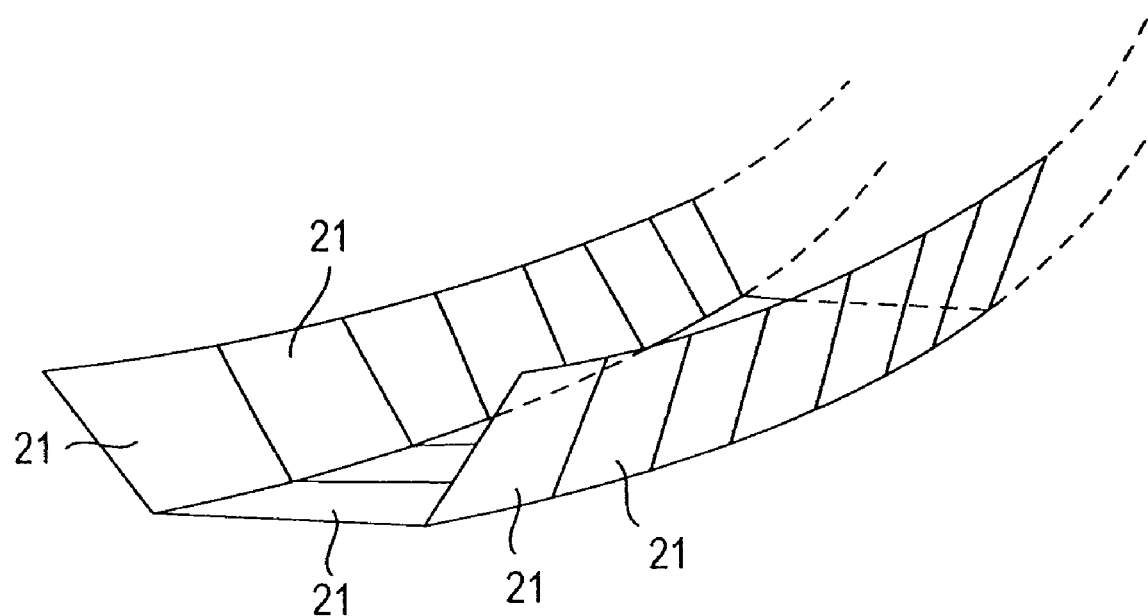
FIG. 4 is a perspective view of a semi-circular trough shaped detector array.
Figure 5:
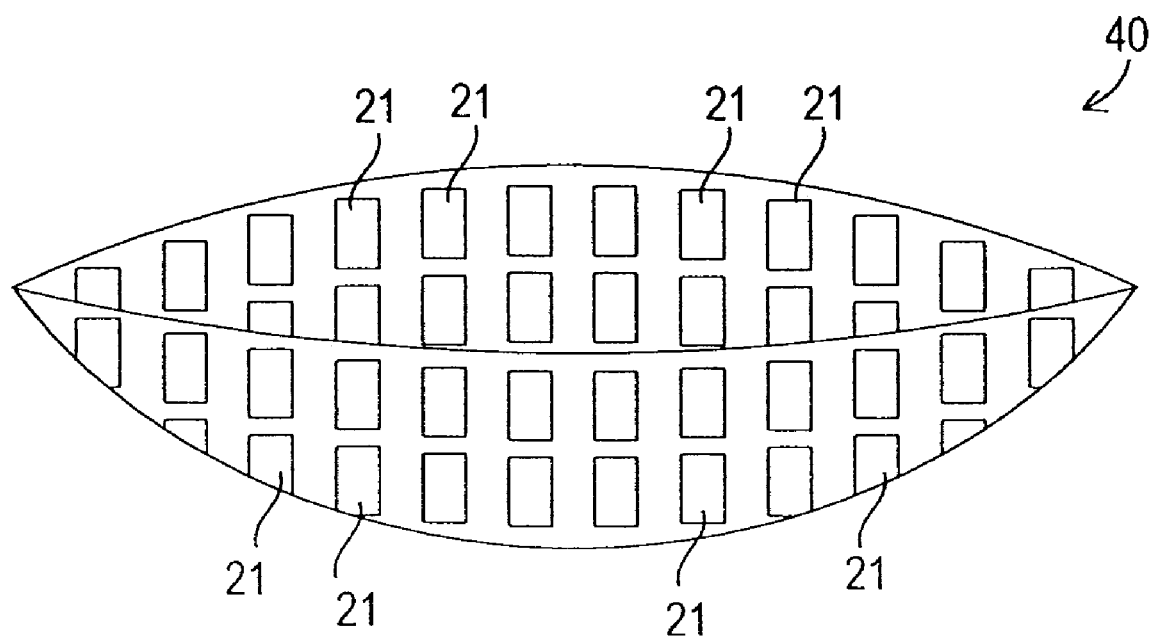
FIG. 5 is a perspective view of a dish shaped detector array.

The detector array 20 may also be shaped like a semicircular trough 38, as shown in FIG. 4, where three rows of detector modules 21 are provided. The detector array 20 may also have a dish shaped configuration 40, as shown in FIG. 5, for example. The dish shaped detector array 40 may comprise 30×15 rows of detector modules 21, and be shaped like an oval. The oval may extend over a sphere of 180 degrees×90 degrees, for example. The detector array 20 may be a flat, as well. The preprocessing and reconstruction algorithm can correct for the use of a flat detector array.

The spatial detector modules 21 may be amorphous Silicon ("aSi") detectors, for example. Each detector module 21 may be a two dimensional detector, with a width of at least about 20-30 cm, for example. The pixel size may be up to 0.5 cm., for example. The detector module 21 may be a 40 cm×30 cm aSi detector available from Varian, for example under the tradename PaxScan™ 4030, for example. The detectors may be coupled to signal processing circuitry comprising a preamplifier stage with dynamically controllable signal gain, as described in U.S. Ser. No. 09/978,727, assigned to the assignee of the present invention and incorporated by reference, herein. Each detector module 21 may be placed end to end, as shown in FIG. 1.

In one example, to scan a cargo container 14 with dimensions of 20×8×8 feet (6.1×2.4×2.4 meters), carried by a truck 12, thirty-five (35) detector modules 21 each having dimensions of 40 cm×30 cm, may be arranged in a semicircle extending over an arc d of 210 degrees to form a detector array 20 having a width W of 30 cm and having an arc length of 14 meters. The beams from each of the six X-ray source 16 may be collimated into a cone beam having a width W of about 30 cm and a length of at least about 233 cm (1400 cm/6). Each cone beam may have a length of up to about 350 cm, for example, to illuminate one detector module 21 and up to about half of the adjacent detector modules or regions of the detector array 20 to ensure that all the detector modules 21 are illuminated. Each cone beam may extend laterally over an arc of about 30 degrees and longitudinally over an arc of about 2 degrees to about 15 degrees, dependent on the size of the detector array 20.

In this embodiment, the X-ray sources 16, the rail 18 and the conveyor system 24 are in the upper portion of the scanning unit 10 and the detector array 20 is in the lower portion, as shown in FIG. 1 and FIG. 2. The detector array 20 may be placed in and supported, in whole or in part by, a semi-circular hole in the ground G beneath the transport system 24, as shown in FIG. 1, to provide a narrow, compact structure for the scanning unit. In such a configuration, the ground absorbs much of the radiation, decreasing the amount of shielding required. A radiation dump is not required. The walls 11 above the ground G are appropriately shielded to absorb scattered radiation, as is known in the art. The positions of the detector array 20 and the sources 16 may be reversed and appropriate additional shielding and a radiation dump provided as necessary.

Figure 6:
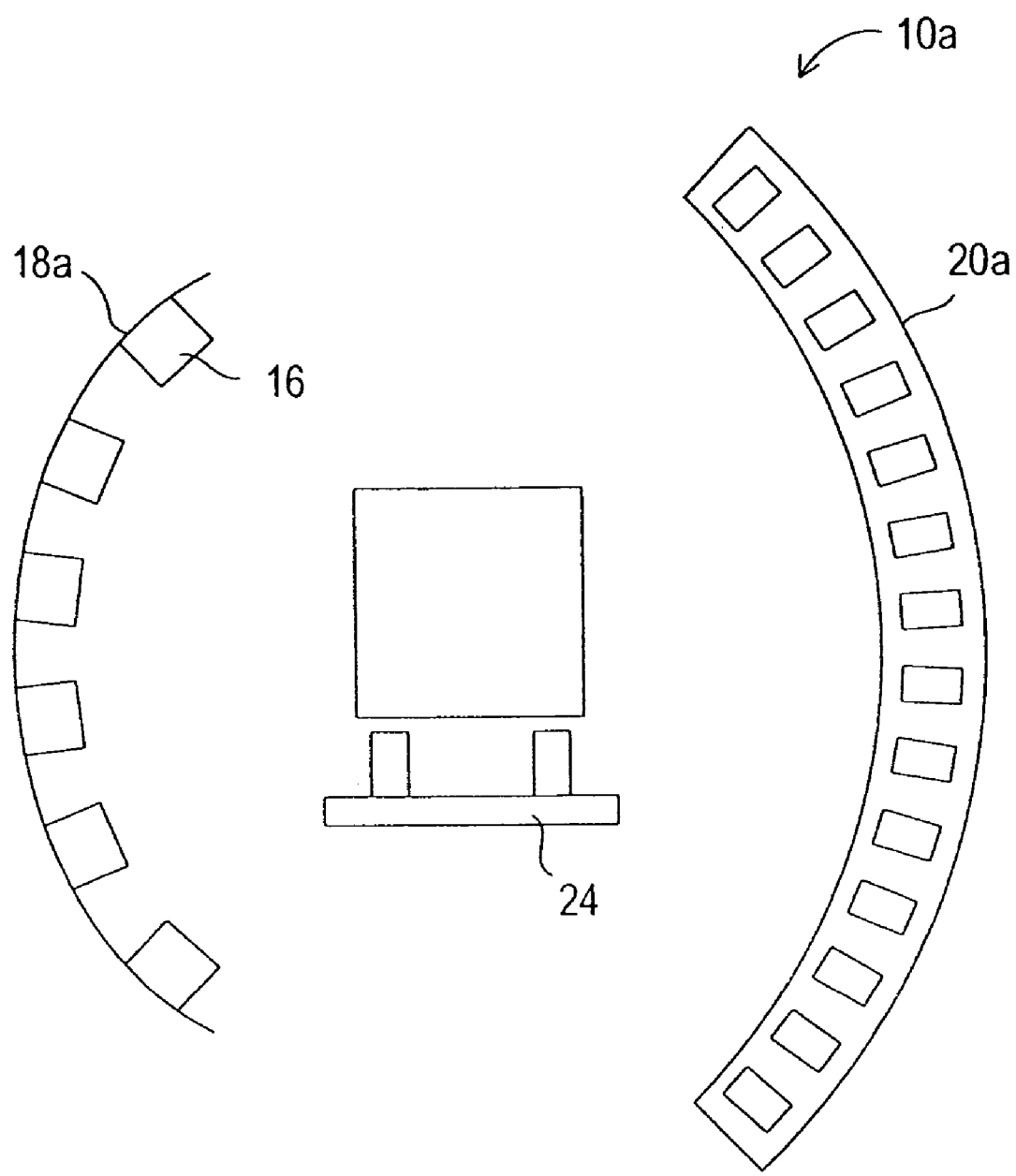
FIG. 6 is a front view of another cargo scanning unit in accordance with an embodiment of the invention, wherein the X-ray sources are on one side of the path traversed by a truck carrying a cargo container and the detectors are on the other side.
Figure 7:
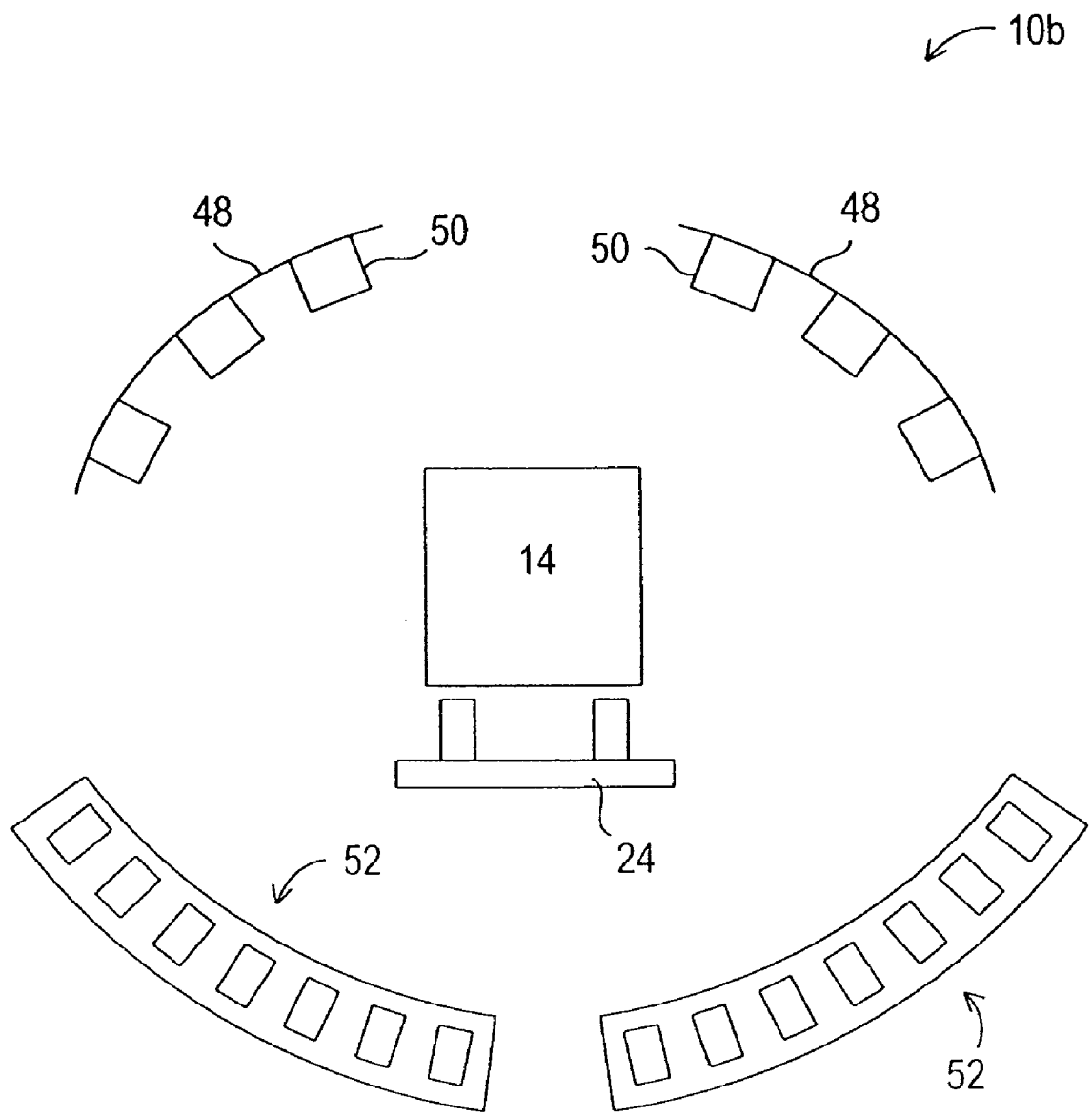
FIG. 7 is a top view of another cargo scanning unit in accordance with an embodiment of the invention, wherein sources and detectors are provided on both sides of the path traversed by a truck carrying a cargo container.

Alternative configurations are possible. FIG. 6 is a front view of a cargo scanning unit 10a, wherein a rail 18a supporting X-ray sources 16 is on one side of the path A traversed by the truck 12 carrying the cargo container 14 and the detector array 20a is on the other side. Shorter rails 48 supporting half of the X-ray sources 50 and shorter detector arrays 52 may also be provided on opposite sides of the cargo container 14 to be scanned, as well, as shown in the front view of a scanning unit 10*b* in FIG. 7.

Returning to FIG. 1, in use, a truck 12 carrying a cargo container 14 or cargo to be examined is transported through the scanning unit by the transport system 24 at a speed about 0.10 feet per second. The X-ray sources 16 and/or the rail 18 are advanced in a continuous motion across an arc of about 210 degrees in about 10 seconds. X-ray cone beams are transmitted through the cargo container 14 by each of the sources 16. Radiographs of the cargo container 14 are taken at each position of each source 16.

A sufficient number of radiographs may be taken at uniformly spaced angular positions of the sources 16 to perform computed tomography ("CT"). CT may be performed with from about 50 to about 2000 projections per imaging volume where each projection is at a slightly different angle. It is believed that 420-720 projections will provide good results. The imaging volume is the section of the cargo container 14 (and optionally the truck 12) that is scanned in a single sweep of the sources 16*a*-16*f* across the rail 18. Images are derived as each source 16*a*-16*f* is moved continuously around the rail 18, while the truck 12 is being moved through the scanning unit 10. Data may be collected as the sources 16*a*-16*f* are moved every 0.5 degrees, for example. Cone beam reconstruction algorithms, such as a Feltkamp algorithm, may be used to reconstruct axial cross-sectional images of the cargo, as is known in the art.

As discussed above, in order to obtain a complete data set for CT reconstruction, where the cone beam has a lateral arc of about 30 degrees, either the sources 16*a*-16*f* should be moved across an arc or the detector array 20 should extend over an arc, equal to about 210 degrees. The arc of the other component should then be 180°. Alternatively, the arc of both may be about 200°.

In cone beam CT systems having a single source and a single detector, an equal number of rays are transmitted from the source to a detector element through each voxel of the object being scanned and the rays have a uniform angular distribution. This data is used by the cone beam reconstruction algorithm to reconstruct an image. In a multi-source cone beam CT system, however, an equal number of rays are not transmitted through each voxel. In addition, the angular distribution of the rays is only approximately uniform. A pre-processing algorithm may therefore be used to select, weight and process the raw data to compensate for the deviations, so the data may be used in the reconstruction algorithm.

The pre-processing algorithm may also compensate for other aspects of the geometry and configuration of the system 10. For example, ideally, the distance from each source 16 to the detector module 21 of the detector array 20 upon which that source aims its cone beam, is as close to a constant distance as possible. Since each detector module 21 is flat, however, the distance will not be constant in this configuration. The pre-processing algorithm may compensate for the deviation in distance. The pre-processing algorithm may also correct for the space between adjacent detector modules 21 in the detector array 20. As mentioned above, if the cone beams overlap on the detector array 20, corrections are required to properly select and weight the collected data. For example, data collected from portions of the detector array where beams overlap may be summed and averaged. These and other required corrections may be derived based on techniques known in the art for cone beam reconstruction where a single source is used.

One scan by each source 16*a*-16*f* may produce about 30 cross-sectional images over 15 centimeters of axial length. Each scan may require about 10 seconds. It may take about 5-10 minutes to conduct CT scanning of an entire cargo container having width and length of about 15 feet×20 feet, for example. A spatial resolution as good as a few millimeters may be obtained. The cargo container 14 may be exposed to a nominally acceptable dose levels, such as 50 Rads, for example.

To increase the scanning rate, a pre-scanning test may be conducted on the cargo to identify suspicious regions of the cargo container 14. CT scanning may then be conducted on the suspicious portions. Trucks carrying cargo without suspicious regions may be cleared more quickly. Trucks with suspicious regions may also be scanned more quickly, since CT scanning is only performed on the suspicious regions.

For example, the scanning unit of FIG. 1 can perform a line scan of the cargo. The X-ray sources 16 are centered over the cargo container 14 by the conveying system 22. Once centered, they need not be moved. The detector array 20 acts as a line detector. Radiographs of the cargo container 14 are reconstructed as the truck 12 passes through the cargo scanning unit 10 at a much higher rate. Radiographs of the entire cargo container 14 may be performed in less than one minute.

Two line scans may be performed along orthogonal scanning directions. The first line scan may be conducted with the sources 16 at one extreme position on the rail 18, such as the leftmost position, as shown in FIG. 1. Then the sources are moved to the opposite extreme position on the rail 18, in this example their rightmost position. The second line scan may then be performed. Additional scans may be conducted with the sources at intermediate positions between the two extremes, as well. Alternatively, the two scans may be performed with the first and last sources 16*a*, 16*f*, simultaneously.

The radiographs may be inspected visually or analyzed by the computer 26 to identify suspicious regions based on the shape, size and density of objects in the radiographs. If suspicious regions are identified, then the transport system 24 can be reversed and the X-ray sources 16 moved to conduct CT scanning of the suspicious regions as the cargo container 14 is moved back through the scanning unit 10, for more detailed, three dimensional views of the suspicious regions of the cargo.

Other pre-screening techniques may be used, as well. For example, more rapid scanning may be conducted by moving the sources 16*a*-16*f* across the rail 18 as the truck 12 is moved along the path A, and taking less than 300 projections. Taking 100 projections, for example, could be about 5 times faster than taking 500. The cone beam reconstruction algorithm may be used to reconstruct the data. The resulting images may be sufficient for an operator or a computer to identify suspicious regions for more detailed examination. As above, CT may then be conducted on the suspicious regions.

Scattered radiation resulting from pencil beam scanning may also be used in pre-scanning. A collimator may be moved in front of each source to define the pencil beam. Operation of the sources 16*a*-16*f* is cycled. One source may be on at a time or sources transmitting beams that do not overlap on the detector array 20 may be on at the same time. Data from detector modules 21 aligned with each transmitted beam may be rejected, so that only scattered radiation is processed. Scanning may be conducted quickly. As above, the resulting images may be sufficient for an operator or a computer to identify suspicious regions for more detailed examination and CT scanning may then be conducted on any suspicious regions.

A pencil probe beam may also be used instead of or along with cone beam (or fan beam) scanning of suspicious regions, identified in pre-screening. The sources 16a-16f may be moved along the rail as the truck 12 is moved by the conveying system 24 to enable the pencil beam or beams to scan the suspicious region from a plurality of angles. Pencil beams are particularly advantageous in scanning small objects.

Scattered radiation need not only be used in pre-scanning. Additional information that may contribute to the identification of contraband within the cargo container 14 may be obtained by detecting radiation scattered by the contents of the container. Additional detectors (not shown) may be provided between the sources 16a-16f and the cargo container 14 to detect back scattered radiation. Alternatively or in addition to the back scatter detectors, additional detectors may be provided at the sides of the cargo container 14 to detect side scattered radiation. The detector array 20 of FIG. 1 can also be used to detect scattered radiation by scanning the cargo container 14 with one source 16 at a time. Radiation transmitted through the cargo container 14 would be detected by the detector or detectors 21 upon which the cone beam is aimed. The other detectors 21 of the detector array 20 will detect scattered radiation.

Additional information useful in identifying contraband may also be obtained by selectively detecting transmitted energy in different energy ranges. Filters (not shown) may be selectively provided in front of the detector array 20 to improve the energy sensitivity of the detector array 20 for a particular energy range. For example, the filters may be configured to block radiation transmitted through the cargo below a certain threshold. An example of a detector that is sensitive over a broad energy range and may be used in the present invention is described in U.S. Ser. No. 10/013,199, filed on Nov. 2, 2002, assigned to the assignee of the present invention and incorporated by reference, herein. Scintillation based detectors comprising photo-multipliers, semiconductor based detectors and gas ionization based detectors sensitive to particular energy ranges are commercially available.

As is known in the art, the interaction of X-ray radiation with different materials, including contraband such as explosives, is dependent on the energy of the X-ray radiation. Additional information useful in identifying contraband may therefore also be obtained by scanning the cargo with two or more different energy distributions having different average energies. The detector array 20 shown in FIG. 1 may be used to detect radiation transmitted through the cargo container 14 at each of the energy distributions. One of the energy distributions may be one with an average energy in which the primary interaction of the X-ray radiation with the cargo is Compton scattering. The other energy distributions may have progressively higher average energies that will cause progressively more pair production and less Compton scattering.

For example, two energy distributions may be provided by X-ray sources with accelerating potentials of 6 MV and 18 MV or higher, respectively. At 6 MV, the X-ray radiation will cause Compton scattering. There is not much pair production. At 18 MV or higher, more pair production is induced. Compton scattering takes place as well.

Different X-ray sources emitting X-ray radiation with different average energies may be used, requiring double the number of sources in the configuration of FIG. 1. Alternatively, each source 16a-16f may be configured to selectively emit X-ray radiation at two or more different energy distributions. Linear accelerators that can emit X-ray radiation at two or more different energy distributions are described in U.S. Pat. No. 6,366,021 B1, U.S. Pat. No. 4,382,208 and U.S. Pat. No. 4,400,650, for example, which are assigned to the assignee of the present invention and are incorporated by reference, herein. The energy distribution of the X-ray beam may be rapidly changed, under the control of the computer 26, in order to scan at both energy distributions when the sources 16 are at each scanning location.

Figure 8:
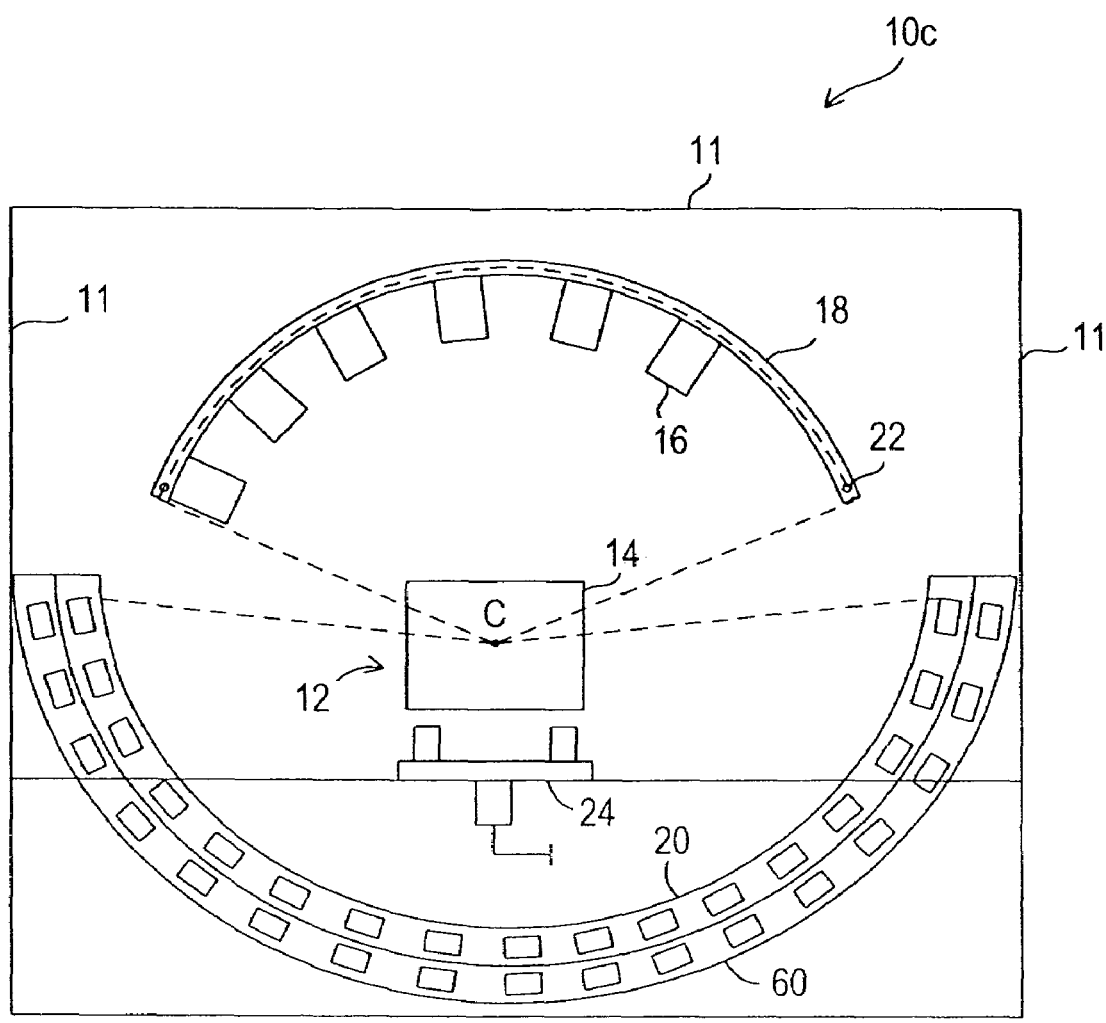
FIG. 8 is a schematic representation of a configuration of a cargo scanning unit including a plurality of X-ray sources that can emit X-ray radiation having more than one energy distribution and an energy sensitive detector array.

As mentioned above, the detector array 20 of FIG. 1 may comprise spatial detectors that detect the radiation transmitted through the cargo container 14 at each energy distribution. Alternatively, energy sensitive detectors may be provided. FIG. 8 is a schematic representation of a configuration of a cargo scanning unit 10c including a plurality of X-ray sources 16 under the control of the computer 26 (not shown in this view) that can emit X-ray radiation having more than one energy distribution. Elements common to the configuration of FIG. 1 are commonly numbered. A second detector array 60 is provided, comprising one or more rows of two dimensional energy sensitive detectors, behind the first detector array 20. The second detector array 60 is responsive to the energy of the X-ray energy transmitted through the cargo container 14 and through the first detector array 20. A sufficient amount of X-ray energy will pass through the first detector array 20 to be detected by the second detector array 60. (While spaces are shown between the detectors 21 and the detector array in FIG. 1 and FIG. 8, the adjacent detectors 21 may be in contact.) Instead of providing a separate energy sensitive detector array 60, two dimensional energy sensitive detectors may also be provided among the two dimensional detectors of the first detector array 20. Filters may be provided between the detector arrays to remove radiation below a certain threshold, to improve the sensitivity of the every sensitive detector array to higher energies, if desired.

Radiographs may be generated, as described above. CT images may also be reconstructed from a sufficient number of radiographs, as well. The energy distribution with the higher average energy may be used to generate the radiographs and CT images.

The detectors 61 of the second detector 60 array may each comprise a scintillator coupled to a photomultiplier tube, for example, as is known in the art. X-ray photons impinging upon the scintillator cause the emission of light photons energies proportional to the energy of the X-ray photons. The light photons are detected by the photomultiplier tube, whose output is proportional to the energy of the detected light photons. Pulse Height Analysis ("PHA") may be used to analyze the data from the energy sensitive detectors. The scintillator may be a cesium iodide, sodium iodide, calcium tungstate, or bismuth germanate scintillator, for example.

Whether only the single detector array 20, as in FIG. 1, or an energy sensitive detector array 60 is also provided, images may be prepared based on data collected at both average energies. Two data points are available at each voxel, each one derived from scanning with a respective energy distribution. The data point derived from scanning at the lower average energy is primarily based on the effects of Compton scattering, which is dependent on the atomic number Z of the material (or materials) in the voxel. The data point derived from scanning at the higher average energy is based on pair production, which is dependant on $Z^2$, as well as Compton scattering. If additional average energies are also used, more data is available that may provide further information about the contents of the cargo container 14. While some of the information is correlated to the information obtained through the use of two energies, the additional information may still be statistically significant. Image contrast may be improved, as well.

Images may be reconstructed based on the scans at each energy level. The images may be compared visually or by the computer 26. The values in all or some of the voxels of the cargo container at each average energy may also be compared or processed to derive information indicative of the material content of the cargo in the voxel. For example, a ratio of the two data points at each voxel yields a value dependent on the average Z and average $Z^2$ of the material in the voxel. The ratio may be compared by the computer 26 to a database corresponding ratios with materials to identify the material in the voxel. U.S. Pat. No. 4,149,081, for example, discusses the analysis and viewing of data sets derived from different energy levels, in a manner generally applicable here. U.S. Pat. No. 4,194,081 is assigned to the assignee of the present invention and is incorporated by reference herein.

Both data points are also dependent on the density of the material in the voxel. The total density of the material may be useful in identifying contraband (explosives, nuclear material and illegal drugs, for example). However, the density of the material may be readily modified by mixing in fillers of different densities, without changing the deleterious characteristics of the contraband. The change in density may make a dangerous explosive appear like an innocuous material on a radiograph. The value of the ratio (average Z/average $Z^2$), however, is independent of the density, making it harder to subvert the system.

Other mathematical combinations of the values may be useful, as well, as is known in the art. The voxel value based on a radiograph at one or both energy levels may also be used in the data analysis.

The images derived from the second, energy sensitive detector array 60, while providing material content information, has low resolution. Corresponding radiograph/CT images derived from data collected by the first detector array 20, which have high resolution, and the images derived from data from the second detector array 60 may also be fused, voxel by voxel, to yield an image with high spatial resolution that also indicates the material content of the voxel. The position, size and shape of suspicious material, as well as the identity of the material, may then be analyzed visually or by the computer 26.

The computer may implement software programs that automatically analyze the images or the image data to identify suspicious objects or materials, as is known in the art. Software may also be used to enhance the displayed image to facilitate visual analysis by an operator. For example, edge enhancement programs may be used, color may be added to identify certain types of materials and surface rendering may be provided, to make objects more recognizable, as is known in the art.

While the invention is particularly suited for scanning cargo containers for contraband, the invention may be readily adapted to scan other objects, as well, such as luggage and carry-on bags in airports.

In addition, while a plurality of sources is shown in FIG. 1, a single source may also be used. The single source may be rapidly moved across the rail 18 by the conveying system 22.

Furthermore, while an X-ray source is described in the examples above, the source or sources may provide other types of radiation, such as a neutron beam, for example.

One of ordinary skill in the art will recognize that other changes may be made to the embodiments described herein without departing from the scope of the invention, which is defined by the claims, below.

We claim:

1. A scanning system for examining contents of an object movable along a first path, the scanning system being positioned, at least in part, above an opening in the ground, the system comprising:
    one or more sources of radiation, at least one of the one or more sources being movable along a single, second path transverse to the first path, the second path extending at least partially around the first path; and
    a detector extending partially around the first path, the detector being positionable at least partially in the opening in the ground and to detect radiation interacting with the object during scanning;
    wherein the at least one source and the detector are positioned so that the object is transportable along the first path, between the source and the detector.

2. The scanning system of claim 1, wherein the object is supported by a vehicle; and
    the detector and the at least one source of radiation are positioned to allow the object and the vehicle to be transported therebetween.

3. The scanning system of claim 1, wherein, during operation:
    the detector is positionable, at least in part, beneath the first path, below ground; and
    the at least one source is positionable above the first path.

4. The scanning system of claim 1, wherein the second path is arcuate.

5. The scanning system of claim 4, further comprising:
    an arcuate rail along the arcuate second path;
    wherein the at least one source is coupled to the arcuate rail.

6. The scanning system of claim 5, wherein the at least one source is movable with respect to the rail.

7. The scanning system of claim 5, wherein the rail is movable to move the at least one source along the second path.

8. The scanning system of claim 5, wherein the arcuate rail forms at least part of a circle.

9. The scanning system of claim 4, wherein the second path is at least partially circular.

10. The scanning system of claim 1, comprising at least one energy sensitive detector.

11. The scanning unit of claim 1, further comprising a processor electrically coupled to the detector, the processor being programmed to reconstruct computed tomography images based, at least in part, on data received from the detector.

12. The scanning system of claim 11, wherein:
    the second path and the detector extend sufficiently around the object to collect sufficient data for computed tomographic imaging.

13. The scanning system of claim 1, further comprising a transport system to convey the object through the scanning unit, along the first path.

14. The scanning system of claim 1, wherein each of the at least one sources is a linear accelerator.

15. The scanning system of claim 1, wherein the at least one source is mechanically movable across the second path.

16. The scanning system of claim 15, comprising:
    a plurality of sources, each mechanically movable across the single path.

17. The scanning system of claim 1, wherein the detector is stationary.

18. The scanning system of claim 1, wherein the at least one source is adapted to generate radiation of at least 1 MeV.

19. The scanning system of claim 1, wherein:
the object is a cargo container; and
the at least one source and the detector are positioned to scan a cargo container having a height and/or width of at least about 1.5 meters.

20. The scanning system of claim 1, wherein the at least one of the one or more sources are adapted to scan the object with two different energy distributions.

21. The scanning system of claim 20, wherein at least one of the one or more sources are operational to selectively switch between emitting radiation having a first energy distribution and radiation having a second energy distribution different than the first energy distribution.

22. The scanning system of claim 20, wherein at least one of the one or more sources emits radiation having a first energy distribution and at least one of the one or more sources emits radiation having a second energy distribution different than the first energy distribution.

23. The scanning system of claim 20, further comprising a second, energy sensitive, detector;
wherein the first detector is between the second detector and the at least one source.

24. The scanning system of claim 23, further comprising a processor electrically coupled to the first detector and the second detector, the processor being programmed to:
reconstruct computed tomography images based on data received from the first detector;
reconstruct energy based images based on data received from the second detector; and
fuse the images based on data from the first detector with the images based on the data received from the second detector.

25. The scanning system of claim 1, wherein the detector is positioned to detect radiation transmitted through the object.

26. The system of claim 1, wherein the detector is positioned, at least in part, in the opening in the ground, during operation.

27. The system of claim 26, wherein the single second path is, at least in part, above the opening in the ground.

28. The scanning unit of claim 1, wherein:
the detector has an arcuate shape;
a portion of the ground in the opening has a shape matching the arcuate shape of the detector; and
a portion of the detector that is positionable in the opening is positioned adjacent the arcuate shaped portion of ground, during scanning.

29. A method of examining contents of an object, comprising:
moving at least one radiation source along a continuous two-dimensional path extending only partially around an object;
scanning at least a portion of the object with at least one radiation beam from the at least one radiation source at a plurality of angles;
detecting radiation interacting with the object by a detector positioned at least partially below ground; and
reconstructing images based, at least in part, on the detected radiation from the at least one radiation source along the continuous two-dimensional path.

30. The method of claim 29, further comprising:
processing data based on the detected radiation to form computed tomographic images of at least the portion of the object.

31. The method of claim 29, comprising:
moving the at least one source in a first direction along the two-dimensional path; and
moving the object along a second path in a second direction transverse to the first direction.

32. The method of claim 29, wherein the detector is a stationary detector, the method further comprising:
detecting radiation transmitted through the object by the stationary detector.

33. The method of claim 29, comprising:
scanning the object with a radiation beam having a first energy distribution; and
scanning the object with a radiation beam having a second energy distribution different from the first energy distribution.

34. The method of claim 33, comprising:
detecting radiation with a first, spatial detector;
detecting radiation with a second, energy sensitive, detector; and
processing data based on the detected radiation from the first and second detectors to form respective computed tomographic images of the object.

35. The method of claim 34, comprising:
fusing corresponding computed tomographic images from the radiation detected from the first and second detectors.

36. The method of claim 29, wherein the object is a cargo container, the method comprising scanning a cargo container having a height and/or width of at least about 1.5 meters.

37. The method of claim 36, wherein the cargo container is supported by a vehicle during scanning.

38. The method of claim 29, comprising:
moving the at least one source along a single arc extending only partially around the object.

39. The method of claim 29, comprising:
moving the at least one radiation source along a rail.

40. The method of claim 39, wherein:
the rail extends only partially around the object.

41. A scanning unit for examining contents of a cargo container movable along a first path, the scanning unit comprising:
a plurality of sources of radiation, at least some of the plurality of sources being configured to irradiate the cargo container with a cone beam of radiation and being movable along a continuous second path transverse to the first path, the second path being semi-circular and extending at least partially around the first path; and
a semi-circular detector extending at least partially around the first path, the detector being positioned to detect radiation interacting with the cargo container during scanning;
wherein:
the second, semi-circular path lies along a first imaginary circle;
the semi-circular detector lies along a second imaginary circle larger than the first imaginary circle;
the first imaginary circle lies, at least in part, within the second imaginary circle; and
the at least some of the plurality of sources and the detector are positioned so that the cargo container is transportable along the first path, between the at least some of the plurality of sources and the detector.

42. A scanning unit for examining contents of a cargo container movable along a first path, the scanning unit comprising:
- one or more sources of radiation configured to generate at least one cone beam of radiation, at least one of the one or more sources being movable along a two-dimensional second path substantially transverse to the first path, the second path extending at least partially around the first path; and
- a first, spatial detector extending at least partially around the first path, the detector being positioned to detect radiation from the at least one of the one or more sources of radiation along the two-dimensional second path, interacting with the cargo container during scanning;
- a second, energy sensitive detector extending at least partially around the first path, the detector being positioned to detect radiation from the at least one of the one or more sources of radiation along the two-dimensional second path, interacting with the cargo container during scanning; and
- a processor to fuse images derived from the first, spatial detector with images derived from the second, energy sensitive detector;
- wherein the at least one source and the first and second detectors are positioned so that the cargo container is transportable along the first path, between the one or more sources and the first and second detectors.

43. The scanning unit of claim 42, wherein the first detector is between the second detector and at least one of the at least one source.

44. A scanning unit for examining contents of an object movable along a first path, the scanning unit comprising:
- one or more sources of radiation, at least one of the one or more sources being movable along a continuous two-dimensional second path substantially transverse to the first path, the second path being semi-circular and extending only partially around the first path; and
- a stationary detector extending only partially around the first path, the detector being positioned to detect radiation, from the one or more sources along the continuous two-dimensional second path, interacting with the object during scanning;
- wherein:
- the second, semi-circular path lies along a first imaginary circle;
- the semi-circular detector lies along a second imaginary circle larger than the first imaginary circle;
- the first imaginary circle lies, at least in part, within the second imaginary circle;
- the at least one source and the detector are positioned so that the cargo container is transportable along the first path, between the one or more sources and the detector; and
- both the second semi-circular path and the semi-circular detector extend over respective arcs, each arc being greater than 180 degrees, to collect sufficient data for computed tomographic reconstruction.

45. The scanning unit of claim 44, wherein the second semicircular path extends over an arc of at least 210 degrees.

46. The scanning unit of claim 44, wherein the detector extends over an arc of at least 210 degrees.

47. The scanning unit of claim 44, wherein the second semicircular path and the detector each extend over an arc of 200 degrees.

48. A scanning unit for examining contents of an object movable along a first path, the scanning unit comprising:
- a rail transverse to the first path;
- a plurality of sources of radiation coupled to the rail, at least some of the plurality of sources being movable along a second path transverse to the first path along the rail;
- a detector array positioned to detect radiation interacting with the object during scanning, the detected radiation originating from at least certain of the plurality of sources along the rail;
- wherein:
- the plurality of sources and the detector array are positioned so that the object is transportable along the first path, between the plurality of sources and the detector array; and
- one or more of the at least certain sources are configured to emit radiation beams that partially overlap at least one respective radiation beam emitted by an adjacent radiation source on a portion of the detector array;
- the scanning unit further comprising a processor configured to turn on at the same time only those radiation sources of the one or more of the at least certain sources that emit radiation beams that do not overlap on portions of the detector array, during scanning.

49. The scanning unit of claim 48, wherein the second path extends only partially around the first path.

50. The scanning unit of claim 48, wherein the second path is a two dimensional path and the rail is configured to move the at least some of the plurality of sources along at least one dimension of the two-dimensional path.

51. The scanning unit of claim 48, wherein:
- the processor is configured to turn on alternate ones of the one or more of the at least certain sources at the same time.

52. The scanning unit of claim 51, wherein the processor is configured to turn on a first set of non-adjacent sources at first times and a second set of non-adjacent sources at second, different times, as the sources are moved across the second path.

53. The scanning unit of claim 48, wherein the detector is arcuate.

54. The scanning unit of claim 48, wherein the second path is arcuate.

* * * * *